United States Patent

Rault et al.

[11] Patent Number: 5,900,247
[45] Date of Patent: *May 4, 1999

[54] MUCOADHESIVE PHARMACEUTICAL COMPOSITION FOR THE CONTROLLED RELEASE OF ACTIVE PRINCIPLES

[75] Inventors: Isabelle Rault, Saint Lye la Foret; Gérald Pichon, Orleans, both of France

[73] Assignee: Adir et Compagnie, Courbevoie, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/777,306

[22] Filed: Dec. 27, 1996

[30] Foreign Application Priority Data

Dec. 29, 1995 [FR] France .................. 95 15701

[51] Int. Cl.⁶ ........................................ A61K 9/70
[52] U.S. Cl. ........................................ 424/434; 424/435

[58] Field of Search ................... 424/434, 435, 424/422; 514/2, 57, 60, 772.1, 773, 778, 780, 781

[56] References Cited

U.S. PATENT DOCUMENTS 4,533,540  8/1985  Blank ......................................... 424/28
5,527,545  6/1996  Santus et al. ............................ 424/490

FOREIGN PATENT DOCUMENTS 0 262 422  4/1988  European Pat. Off. ......... A61K 9/24
1268630   10/1989  Japan .

*Primary Examiner*—Lynette F. Smith
*Assistant Examiner*—Brenda G. Brumback
*Attorney, Agent, or Firm*—The Firm of Gordon W. Hueschen

[57] ABSTRACT

The present invention relates to a new mucoadhesive pharmaceutical composition which makes possible the prolonged release of active pharmaceutical principles in the buccal cavity or via the transmucosal route.

13 Claims, No Drawings

MUCOADHESIVE PHARMACEUTICAL COMPOSITION FOR THE CONTROLLED RELEASE OF ACTIVE PRINCIPLES

BACKGROUND OF THE INVENTION

The present invention relates to a new bioadhesive pharmaceutical composition which makes possible the controlled release of active principles locally in the buccal cavity or systemically through a buccal (jugal or gingival), perlingual, nasal, vaginal or rectal mucus membrane. The pharmaceutical composition according to the invention ensures a more or less rapid release of the active principle and can remain attached for a more or less lengthy period of time to the buccal (jugal and gingival mucus membrane), perlingual, nasal, vaginal and rectal mucus membrane.

TECHNICAL FIELD

Administration via the transmucosal route has the advantage, at the metabolic level, of avoiding significant metabolization of the active principle by the hepatic first-pass effect and thus, at the clinical level, of decreasing the doses administered by improving the therapeutic efficiency. The active principle is not subject to the various enzymatic or chemical degradations present throughout the gastrointestinal tract, nor to the disadvantages related to the functioning and to the physiology of the gastrointestinal apparatus.

The possibilities of administration of an active principle through a mucus membrane depend on various factors. In particular, the composition must not detrimentally affect the tissue in any way following prolonged contact and must not cause irritation, allergies or sensitizations and the active principle must be able to pass through a fairly small tissue surface area at a diffusion rate which is sufficient to produce plasma levels suitable for therapeutic requirements.

A bioadhesive form exhibits the property of adhering to a biological tissue, for example to a mucus membrane in the buccal cavity, i.e., where it is mucoadhesive, and of being maintained there for a more or less lengthy period of time. The bioadhesion phenomenon is described in the literature and is provided by the establishment of binding between one or more compounds of the pharmaceutical dosage form and functional chemical groups present at the surface of the biological tissue. The interactions which are involved in the bioadhesion mechanism are described as being of physical mechanical or chemical nature.

DESCRIPTION OF THE INVENTION

The pharmaceutical composition as claimed in the invention, in addition to the fact that it is novel, makes it possible to obtain a strong bioadhesive effect and a controlled and reproducible release of the active principle.

The bioadhesive pharmaceutical composition of the present invention is characterized by the use:
- of a polymer (A) composed of one or a number of vinyl acetate/polyvinylpyrrolidone copolymers. This excipient, which is commonly used as binder and disintegrating agent in tablets, surprisingly makes possible the formulation of films (or patches) having advantageous bioadhesive properties for transmucosal administration,
- of one or of a number of active principles,
- optionally, of a compound (B) comprising one or a number of compounds, such as cellulose and its derivatives, such as, for example, ethyl cellulose, hydroxypropyl cellulose, hydroxypropyl methyl cellulose, and the like, starches of various origins and their derivatives, gum arabic, gum tragacanth, guar gum, xanthan gum, carob bean gum or carrageenates, and of excipients acting as plasticizers, flavoring agents or sweeteners.

The compound (A) is composed of one or a number of vinyl acetate/polyvinylpyrrolidone copolymers of following formula:

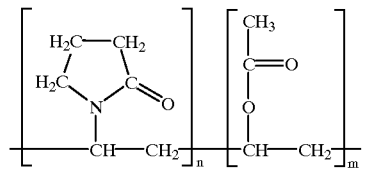

Specific examples of this type of copolymer which are currently available commercially are Kollidon VA64® (BASF) and the copolymers E-335®, E-535®, E-735®, I-235®, I-335®, I-535®, I-735® and S-630® (ISP).

The compound (B), when it is present in the pharmaceutical dosage form according to the invention, makes it possible to prolong the release of the active principle.

The bioadhesion and the controlled release are provided by the compound (A). The proportion of the compound (A) is between 5 and 85% by mass. The type of vinyl acetate/polyvinylpyrrolidone copolymer chosen makes it possible to vary the rate of solubilization: the higher the proportion of polyvinylpyrrolidone, the faster the solubilization. The proportion of the compound (B), if it is present, is between 5 and 85% by mass. The controlled release can be modulated according to the proportions used.

Moreover, vinyl acetate/polyvinylpyrrolidone copolymers are inexpensive, which is reflected in the production of inexpensive pharmaceutical compositions.

The pharmaceutical composition as claimed in the invention is more specifically provided in the form of a bioadhesive matrix system composed of a film with a thickness preferentially of between 0.2 and 3.0 mm.

This type of system is particularly advantageous in comparison with a bioadhesive tablet: indeed, tolerance by the patient can be improved due to the thinness of the system; moreover, the release of active principles of low solubility can be accelerated.

The pharmaceutical dosage form can be circular, rectangular or oblong in shape and can have a surface area preferentially of between 0.1 and 5.0 cm².

Mention may be made, among the plasticizers used, of glycerol, glycerin, Transcutol®, PEG 400, propylene glycol, and the like.

The pharmaceutical dosage form can also contain sweetening excipients, such as sodium saccharinate, and flavoring excipients.

During manufacture, the mixture of the compound (A), the compound (B), the active principle or principles, the excipient acting as plasticizer and the other excipients (for example a flavoring agent) is distributed by spreading or any other process over a biodegradable or nonbiodegradable protective film or over a substrate (glass, stainless steel, and the like). The assembly is dried for a time of between 10 minutes and 2 hours at a temperature of between 30 and 70° C.

The protective film over which the preparation is spread can be chosen for its adhesive or bioadhesive properties and is peelable.

A specific case of a pharmaceutical dosage form can be prepared in the following way: the protective film which covers the matrix part of the buccal patch can in addiction form an adhesive crown around the matrix part.

The pharmaceutical composition with its adhesive crown has the advantage of preventing the departure of the active principle via the sides of the pharmaceutical dosage form, which, in the case of the buccal mucus membrane, for example, makes it possible to increase the fraction absorbed by the transmucosal route.

The pharmaceutical composition as claimed in the invention is characterized in that it is kept applied to the buccal, perlingial, nasal, rectal or vaginal mucus membrane for a period of time ranging from 10 minutes up to 24 hours.

Mention may be made, among the active principles used in the pharmaceutical composition according to the invention, as non-limiting examples, of: anti-infectives, such as penicillins, cephalosporins, cyclines, β-lactamase inhibitors, aminosides, quinolones, nitroimidazols, sulfamides or antibacterials, antihistaminics, antiallergics, anesthetics, steroidal or non-steroidal anti-inflammatories. antalgesics with local or systemic effect, antispasmodics, anticancers, diuretics, β-blockers, antihypertensives, antianginals, antiarrhythmics, vasodilators, bradycardic agents, calcium inhibitors, sedatives, cardiotonics, antifungals, antiulceratives, vasotonics, vasoprotectants, anti-ischemics, antiemetics, antispasmodics, anticoagulants, antithrombotics, immunosuppressants, immunomodulators, antivirals, antidiabetics, hypolipidemics, agents for combating obesity, anticonvulsants, hypnotics, antiparkinsonians, antimigraines, neuroleptics, anxiolytics, antidepressants, psychostimulants, agents for promoting memory, bronchodilators, antitussives, agents for combating osteoporosis, peptide hormones, steroids, enzymes, enzyme inhibitors or melatoninergic agonists or antagonists.

The following examples illustrate the invention but do not limit it in any way.

EXAMPLE 1

0.15 g of dihydroergotamine monomethanesulfonate are dissolved, with 5 g of vinyl acetate/polyvinylpyrrolidone copolymer (of PVP/VA E-735 type, ISP France) (as dry weight), in 10 ml of 50/50 alcohol/0.1N hydrochloric acid solution. The polyvinylpyrrolidone/vinyl acetate copolymer of E-735 type has the following composition: 70% polyvinylpyrrolidone and 30% vinyl acetate. When the mixture is homogeneous, 0.5 g of propylene glycol is added. Stirring is allowed to take place for 30 minutes until a completely homogeneous mixture is obtained.

The mixture obtained is spread over an ethylene/vinyl acetate protective film. The film is dried at room temperature for 2 hours. Disks with a diameter of 1 cm are then cut out using a hollow punch. The thickness of the disks is approximately 0.2 mm.

EXAMPLE 2

0.88 g of dihydroergotamine monomethanesulfonate are dissolved, with 5 g of vinyl acetate/polyvinylpyrrolidone copolymer (of PVP/VA E-735 type, ISP France), in 10 ml of 50/50 alcohol/0.1N hydrochloric acid solution. The vinyl acetate/polyvinylpyrrolidone copolymer of E-735 type has the following composition: 70% polyvinylpyrrolidone and 30% vinyl acetate. When the mixture is homogeneous, 0.5 g of propylene glycol is added. Stirring is allowed to take place for 30 minutes until a completely homogeneous mixture is obtained.

The mixture obtained is spread over an ethylene/vinyl acetate protective film. The film is dried at room temperature for 2 hours. Disks with a diameter of 1 cm are then cut out using a hollow punch.

EXAMPLE 3

0.7 g of dihydroergolamine mesylate are dissolved, with 4.5 g of vinyl acetate/polyvinylpyrrolidone copolymer, in 4 ml of alcoholic solution. The vinyl acetate/polyvinylpyrrolidone copolymer of VA 64 type from BASF has the following composition: 60% polyvinylpyrrolidone and 40% vinyl acetate. When the mixture is homogeneous, 0.15 g of sodium saccharinate is added. 1.00 g of polyethylene glycol 400 and then 0.4 g of a liquid mixture of flavoring agents are then added to the homogeneous mixture.

The mixture obtained is spread over an ethylene/vinyl acetate protective film. The film is dried at room temperature for 2 hours. Disks with a diameter of 1 cm are then cut out using a hollow punch.

EXAMPLE 4

1.0 g of amineptine hydrochloride is dissolved, with 7.46 g of vinyl acetate/polyvinylpyrrolidone copolymer, in 8.75 ml of alcoholic solution containing preservatives. The vinyl acetate/polyvinylpyrrolidone copolymer of VA 64 type from BASF has the following composition: 60% polyvinylpyrrolidone and 40% vinyl acetate. When the mixture is homogeneous, 6.25 ml of an aqueous solution containing 0.24 g of sodium saccharinate are added. 1.5 g of polyethylene glycol 400 and then 0.55 g of a liquid mixture of flavoring agents are then added to the homogeneous mixture obtained.

The mixture obtained is spread over an ethylene/vinyl acetate protective film. The film is dried at room temperature for 2 hours. Disks with a diameter of 1 cm are then cut out using a hollow punch.

EXAMPLE 5

1.0 g of piribedil monomethanesulfonate is dissolved, with 7.31 g of vinyl acetate/polyvinylpyrrolidone copolymer, in 8.75 ml of alcoholic solution containing preservatives. The vinyl acetate/polyvinylpyrrolidone copolymer of VA 64 type from BASF has the following composition: 60% polyvinylpyrrolidone and 40% vinyl acetate. When the mixture is homogeneous, 6.25 ml of an aqueous solution containing 0.24 g of sodium saccharinate are added. 1.5 g of polyethylene glycol 400 and then 0.55 g of a liquid mixture of flavoring agents are then added to the mixture obtained.

The mixture obtained is spread over an ethylene/vinyl acetate protective film. The film is dried at room temperature for 2 hours. Disks with a diameter of 1 cm are then cut out using a hollow punch.

EXAMPLE 6

0.25 g of melatonin is dissolved, with 7.46 g of vinyl acetate/polyvinylpyrrolidone copolymer, in 8.75 ml of alcoholic solution containing preservatives. The vinyl acetate/polyvinylpyrrolidone copolymer of VA 64 type from BASF has the following composition: 60% polyvinylpyrrolidone and 40% vinyl acetate. When the mixture is homogeneous, 6.25 ml of an aqueous solution containing 0.24 g of sodium saccharinate are added. 1.5 g of polyethylene glycol 400 anal then 0.55 g of a mixture of flavoring agents are then added to the mixture obtained.

The mixture obtained is spread over an ethylene/vinyl acetate protective film. The film is dried at room temperature for 2 hours. Disks with a diameter of 1 cm are then cut out using a hollow punch.

EXAMPLE 7

1.0 g of fusafungine is dissolved, with 6.7 g of vinyl acetate/polyvinylpyrrolidone copolymer, in 8.75 ml of alcoholic solution containing preservatives. The vinyl acetate/polyvinylpyrrolidone copolymer of VA 64 type from BASF has the following composition: 60% polyvinylpyrrolidone and 40% vinyl acetate. When the mixture is homogeneous, 1 ml of an aqueous solution containing 0.24 g of sodium saccharinate is added. 1.50 g of polyethylene glycol 400 and then 0.55 g of a mixture of flavoring agents are then added to the mixture obtained. The mixture obtained is spread over an ethylene/vinyl acetate protective film. The film is dried at room temperature for 2 hours. Disks with a diameter of 1 cm are then cut out using a hollow punch.

EXAMPLE 8

1.0 g of fusafungine is dissolved, with 6.7 g of vinyl acetate/polyvinylpyrrolidone copolymer, in 8.75 ml of alcoholic solution containing preservatives. The vinyl acetate/polyvinylpyrrolidone copolymer of VA 64 type from BASF has the following composition: 60% polyvinylpyrrolidone and 40% vinyl acetate. When the mixture is homogeneous, 1 ml of an aqueous solution containing 0.24 g of sodium saccharinate is added. 1.50 g of polyethylene glycol 400 and then 0.47 g of an aromatic composition are then added to the mixture obtained.

The mixture obtained is spread over an ethylene/vinyl acetate protective film. The film is dried at room temperature for 2 hours. Disks with a diameter of 1 cm are then cut out using a hollow punch.

EXAMPLE 9

1.0 g of fusafungine and 1.0 g of lidocaine hydrochloride are dissolved, with 6 g of vinyl acetate/polyvinylpyrrolidone copolymer, in 8.75 ml of alcoholic solution containing preservatives. The vinyl acetate/polyvinylpyrrolidone copolymer of VA 64 type from BASF has the following composition: 60% polyvinylpyrrolidone and 40% vinyl acetate. When the mixture is homogeneous. 1 ml of an aqueous solution containing 0.23 g of sodium saccharinate is added. 1.30 g of polyethylene glycol 400 and then 0.47 g of an aromatic composition are then added to the mixture obtained. The mixture obtained is spread over an ethylene/vinyl acetate protective film. The film is dried at room temperature for 2 hours. Disks with a diameter of 1 cm are then cut out using a hollow punch.

EXAMPLE 10

1.0 g of fusafungine and 0.4 g of lidocaine hydrochloride are dissolved, with 6.6 g of vinyl acetate/polyvinylpyrrolidone copolymer, in 8.75 ml of alcoholic solution containing preservatives. The vinyl acetate/polyvinylpyrrolidone copolymer of VA 64 type from BASF has the following composition: 60% polvinylpyrrolidone and 40% vinyl acetate. When the mixture is homogeneous, 1 ml of an aqueous solution containing 0.23 g of sodium saccharinate is added. 1.30 g of polyethylene glycol 400 and then 0.47 g of an aromatic composition are then added to the mixture obtained. The mixture obtained is spread over an ethylene/vinyl acetate protective film. The film is dried at room temperature for 2 hours. Disks with a diameter of 1 cm are then cut out using a hollow punch.

EXAMPLE 11

0.05 g of betamethasone 17-valerate is dissolved, with 7.66 g of vinyl acetate/polyvinylpyrrolidone copolymer, in 8.75 ml of alcoholic solution containing preservatives. The vinyl acetate/polyvinylpyrrolidone copolymer of VA 64 type from BASF has the following composition: 60% polyvinylpyrrolidone and 40% vinyl acetate. When the mixture is homogeneous, 6.25 ml of an aqueous solution containing 0.24 g of sodium saccharinate are added. 1.50 g of polyethylene glycol 400 and then 0.55 g of a mixture of flavoring agents are then added to the mixture obtained. The mixture obtained is spread over an ethylene/vinyl acetate protective film. The film is dried at room temperature for 2 hours. Disks with a diameter of 1 cm are then cut out using a hollow punch.

EXAMPLE 12

0.11 g of cetylpyridinium chloride are dissolved, with 7.6 g of vinyl acetate/polyvinylpyrrolidone copolymer, in 8.75 ml of alcoholic solution containing preservatives. The vinyl acetate/polyvinylpyrrolidone copolymer of VA 64 type from BASF has the following composition: 60% polyvinylpyrrolidone and 40% vinyl acetate. When the mixture is homogeneous, 6.25 ml of in aqueous solution containing 0.24 g of sodium saccharinate are added. 1.50 g of polyethylene glycol 400 and then 0.55 g of a mixture of flavoring agents are then added to the mixture obtained. The mixture obtained is spread over an ethylene/vinyl acetate protective film. The film is dried at room temperature for 2 hours. Disks with a diameter of 1 cm are then cut out using a hollow punch.

We claim:

1. A mucoadhesive pharmaceutical composition for the controlled release of active pharmaceutical principles in the buccal cavity or through a mucus membrane, which is a solid matrix in which an active pharmaceutical principle is homogeneously dispersed, wherein the mucoadhesion and the controlled release are provided by between 5 and 85% of the total mass of said matrix of a compound (A) consisting of one or a number of vinyl acetate/polyvinylpyrrolidone copolymers, said matrix being in the form of a preformed film having a thickness between 0.2 and 3.0 millimeters and having a surface area between 0.1 and 5.0 square centimeters.

2. The pharmaceutical composition as claimed in claim 1, wherein the matrix contains, in addition to the compound (A), one or a number of active pharmaceutical principles and one or a number oftherapeutically acceptable excipients.

3. The pharmaceutical composition as claimed in claim 2, wherein the active pharmaceutical principle or principles are selected from the group consisting of anti-infectives, penicillins, cephalosporins, cyclines, β-lactamase inhibitors, aminosides, quinolones, nitroimidazoles, sulfamides, antihistaminics, antiallergics, anesthetics, steroidal or non-steroidal anti-inflammatories, analgesics with local or systemic effect, antispasmodics, anticancers, diuretics, β-blockers, antihypertensives, antianginals, antiarrhythmics, vasodilators, bradycardic agents, calcium inhibitors, sedatives, cardiotonics, antifungals, antiulceratives, vasotonics, vasoprotectants, anti-ischemics, antiemetics, anticoagulants, antithrombotics, immunosuppressants, immunomodulators, antivirals, antidiabetics, hypolipidemics, agents for combating obesity, anticonvulsants, hypnotics, antiparkinsonians, antimigraines, neuroleptics, anxiolytics, antidepressants, psychostimulants, agents for promoting memory, bronchodilators, antitussives, agents for combating osteoporosis, peptide hormones, steroids, enzymes, enzyme inhibitors, and melatoninergic agonists or antagonists.

4. The pharmaceutical composition as claimed in claim 2, wherein the therapeutically-acceptable excipient is selected from the group consisting of plasticizers, flavoring agents, and sweeteners.

5. The pharmaceutical composition as claimed in claim 2, wherein mucoadhesion is provided for a period ranging up to 24 hours.

6. The pharmaceutical composition as claimed in claim 1, wherein the matrix contains, in addition to the compound (A), one or a number of active pharmaceutical principles, one or a number of pharmaceutically-acceptable excipients and a material (B) comprising one or a number of compounds selected from the group consisting of cellulose and its derivatives, starches and their derivatives, gums, and carrageenates.

7. The pharmaceutical composition as claimed in claim 6, wherein the pharmaceutically-acceptable excipient is selected from the group consisting of plasticizers, flavoring agents, and sweeteners.

8. The pharmaceutical composition as claimed in claim 6, wherein the amount of the material (B) is between 5 and 85% of the total mass of the composition.

9. The pharmaceutical composition as claimed in claim 6, wherein mucoadhesion is provided for a period ranging up to 24 hours.

10. The pharmaceutical composition as claimed in claim 6, wherein the active pharmaceutical principle or principles are selected from the group consisting of anti-infectives, penicillins, cephalosporins, cyclines, β-lactamase inhibitors, aminosides, quinolones, nitroimidazoles, sulfamides, antihistaminics, antiallergics, anesthetics, steroidal or non-steroidal anti-inflammatories, analgesics with local or systemic effect, antispasmodics, anticancers, diuretics, β-blockers, antihypertensives, antianginals, antiarrhythmics, vasodilators, bradycardic agents, calcium inhibitors, sedatives, cardiotonics, antifungals, antiulceratives, vasotonics, vasoprotectants, anti-ischemics, antiemetics, anticoagulants, antithrombotics, immunosuppressants, immunomodulators, antivirals, antidiabetics, hypolipdemics, agents for combating obesity, anticonvulsants, hypnotics, antiparkinsonians, antimigraines, neuroleptics, anxiolytics, antidepressants, psychostimulants, agents for promoting memory, bronchodilators, antitussives, agents for combating osteoporosis, peptide hormones, steroids, enzymes, enzyme inhibitors, and melatoninergic agonists or antagonists.

11. The pharmaceutical composition as claimed in claim 1, wherein mucoadhesion is provided for a period ranging up to 24 hours.

12. The pharmaceutical composition of claim 1 wherein said film is attached on a surface thereof to a protective film.

13. The pharmaceutical composition of claim 12 wherein said protective film is an ethylene/vinyl acetate film.

* * * * *

UNITED STATES PATENT AND TRADEMARK OFFICE
CERTIFICATE OF CORRECTION

PATENT NO. : 5,900,247
DATED : May 4, 1999
INVENTOR(S) : I. Rault and G. Pichon

It is certified that error appears in the above-indentified patent and that said Letters Patent is hereby corrected as shown below:

Column 1, line 45:  Insert a -- , -- (comma) at the end of the line.

Column 4, line 5:  "dihydroergolamine" should read -- dihydroergotamine --.

Column 4, line 64:  "anal" should read -- and --.

Column 6, line 25:  "in" should read -- an --.

Column 6, line 49:  "oftherapeutically acceptable" should read -- of therapeutically-acceptable --.

Signed and Sealed this

Twenty-third Day of November, 1999

Attest:

Q. TODD DICKINSON

*Attesting Officer*          *Acting Commissioner of Patents and Trademarks*